United States Patent [19]

Hlousek

[11] Patent Number: 5,037,199
[45] Date of Patent: Aug. 6, 1991

[54] BALL LENS MICRO-CELL

[75] Inventor: Louis Hlousek, Reno, Nev.

[73] Assignee: Linear Instruments Corporation, Reno, Nev.

[21] Appl. No.: 314,462

[22] Filed: Feb. 22, 1989

[51] Int. Cl.$^5$ .................... G01N 21/05; G01N 21/85
[52] U.S. Cl. .................... 356/246; 356/410
[58] Field of Search .................... 356/246, 410

[56] References Cited

U.S. PATENT DOCUMENTS

| | | | |
|---|---|---|---|
| 3,497,303 | 2/1970 | Enemark et al. | 356/246 |
| 3,531,211 | 9/1970 | Staunton | 356/246 X |
| 3,556,659 | 1/1971 | Hawes | 356/246 X |
| 4,021,123 | 5/1977 | Atwood et al. | 356/246 X |
| 4,348,107 | 9/1982 | Leif | 356/246 X |
| 4,492,463 | 1/1985 | Marcuse et al. | 356/73.1 |
| 4,714,345 | 12/1987 | Schrader | 356/246 X |
| 4,747,687 | 5/1988 | Hoppe et al. | 356/246 |

Primary Examiner—Vincent P. McGraw
Attorney, Agent, or Firm—Lyon & Lyon

[57] ABSTRACT

There is disclosed herein a cell assembly for use in spectrophotometric analysis or detection of a substance within a small sample volume, such as in a capillary sample cell. The assembly comprises a transparent lens having the shape of a ball, sphere or cylinder, referred to as a "ball lens," and which is placed in direct contact or close proximity to the exterior wall of the capillary cell. This lens and cell are mounted together, any may form a removable cell assembly. The small volume may be contained within the ball lens itself. The ball lens serves to concentrate and direct light into the capillary cell. The arrangement also significantly reduces the sensitivity to alignment of replaceable cells thereby permitting easier mounting and replacement of such cells.

14 Claims, 7 Drawing Sheets

BALL LENS MICRO-CELL

FIELD OF THE INVENTION

The present invention relates to the field of spectroscopy, and more particularly to spectroscopy of samples occupying small volumes.

BACKGROUND

Emerging chromatographic techniques such as high performance capillary electrophoresis, packed capillary liquid chromatography, and super critical chromatography require spectroscopic measurements to be made on extremely small volumes of flowing liquid samples. The typical application has a sample flowing through a fused silica capillary tube with inside diameters ranging from fifteen to one hundred-fifty micrometers and with outside diameters of one hundred-fifty to three hundred micrometers. Various techniques presently are used for directing light from a suitable source into and/or through such a small volume sample cell, as well as taking the light emanating from the inside of the cell and directing it toward a light detecting or analyzing instrument to effect optical analysis or detection of samples contained in the cell. Alignment of the optical system so as to appropriately direct the light from the source to the capillary cell and particularly to the bore and sample therein and/or direct the radiation emanating from the cell to a detector has been a constant problem.

The underlying problem can be generally described as one of directing light from a light source of finite extent to or through a volume of interest that has a cross sectional area perpendicular to the optical axis which is less than that of the source, or directing light that emanates from or passes through a volume of interest to a photodetector or analyzer that has a cross sectional area larger than that of the volume of interest. This is achieved by using a lens or system of lenses to image the source into the volume of interest at a magnification that matches the size of the image to the cross sectional size of the volume of interest or to similarly image the volume of interest onto a photodetector or analyzer. The numerical aperture of the system as viewed from the volume of interest will be greater than the numerical aperture as viewed from the source by a factor of one divided by the magnification. It is generally desired to transfer the greatest possible amount of light from the source to the image by using a low f/number lens system.

SUMMARY OF THE INVENTION

The present invention pertains to using a ball (or cylinder) lens as the highest power optical element in such foregoing situations.

The present invention thus is directed to a relatively simple optical system that takes radiation from a source, concentrates that radiation and directs it to a small volume sample cell (including, but not limited to a sample cell or any volume in which it is desired to make spectroscopic measurements), and likewise can be used for taking the light emanating from the inside of the cell and directing it toward a suitable detector or the like. This is accomplished by using a sphere, truncated sphere, cylinder, or truncated cylinder of suitably transparent refractive material and which therefore forms a ball or cylinder lens; this type of lens being referred to herein as a "ball lens." This lens is placed in close proximity to a sample cell, so that the center line of this lens lies on a line extending from the source, or to a detector as the case may be, to the area of interest in the sample cell. With this lens and the cell being mounted together as a unit, the lens not only appropriately concentrates the light, but also alignment of this assembly in the monitor instrument is substantially less critical. Another embodiment has the sample volume within the ball lens of transparent refractive material and off the axis of the lens such that a center line of the lens lies on a line extending from the source, or to a detector as the case may be, to the area of interest in the small volume.

As noted above, the lens of the present invention is herein generally referred to as a "ball lens," and it is to be understood that this term is used to encompass a spherical ball, cylinder, truncated sphere or truncated cylinder lens. The spacings of the source, ball lens and cell, as well as the index of refraction of the ball lens, are selected according to well known optical techniques to maximize the transference of light from the source into the sample cell or, alternatively, from the sample cell to a suitable detector. Additional optical elements, such as lenses, may be used in between the source or detector and the ball lens. The concepts of the present invention enable the sensitivity to alignment of replaceable cells to be reduced, thereby permitting easier mounting and replacement of the sample cells.

The ball lens acts as a very short focal length lens to convert the slowly converging light (low numerical aperture) from the source to a rapidly converging cone of light (high numerical aperture) that will image the source into or through the area of interest in the sample cell. For emission from the sample cell, the ball lens acts as a very short focal length lens to convert the rapidly diverging cone of light (high numerical aperture) emanating from the sample volume to a slowly diverging cone of light (low numerical aperture) that can be coupled to a suitable light sensing means.

The use of the ball lens to produce a low f/number enables one to achieve what could only be done with a much more complicated and costly optical system involving more optical elements with the inherent greater loss of light as a result of surface reflections and absorption of light in the material of the optical elements. This is particularly significant in ultraviolet applications where light loss due to these effects can be large. With the present invention, a low f/number is less than f/2, more preferably f/1.

As a result of the simplicity and low cost of a ball lens, it can be permanently attached to the small volume in applications where the cell is replaceable and/or disposable. A significant benefit is that the use of the ball lens decreases the sensitivity to alignment between the replaceable cell and the rest of the optical system, as will be discussed in greater detail subsequently, because of the magnification properties of the ball lens and the mounting of this lens adjacent the cell as an integral unit. This makes design, as well as construction of the mounting means, and replacement of the cell easier. For example, if the ball lens is mounted to the fixed part of the instrument and not to the cell, and the cell comprises a one hundred micron inside diameter capillary, the cell would have to be positioned in alignment with the optical axis of the instrument to a tolerance of better than twenty microns (about 0.0008 inch) to insure that most of the light would reach the inside of the capillary. On the other hand, a two millimeter ball lens mounted to the capillary according to the present invention, instead of to a fixed part of the instrument, increases the mounting tolerance to nearly three hundred microns (0.005 inch). Consequently, this reduces the required precision in mounting by a factor of twelve. Although it is preferred for alignment purposes for the ball lens to be fixed to the cell, they can be separate and the ball lens can be part of the instrument.

According to one exemplary embodiment of the present invention, light of a particular wavelength is transmitted through a capillary sample cell in an absorbance monitor. In this embodiment, light of known wavelength emanates from a source. A lens focuses the light onto a synthetic fused silica sphere (the ball lens) that is in contact with the capillary cell. The shape and size of the beam of light may be controlled or selected by placement of one or more suitably shaped apertures on axis with the source and the cell. Light passes through the inside bore of the capillary and the sample contained therein, and continues to a photodetector. The source, aperture, ball lens and photodetector are all part of a fixed instrument, but the ball lens and capillary sample cell are part of a separate removable cell assembly. An aperture may be mounted on the removable cell assembly if desired. In this embodiment, another ball lens may be used to direct the light, after leaving the cell, onto the photodetector. A suitable mounting structure for retaining the ball lens adjacent the capillary to form a removable cell assembly is shown and described later herein.

Another embodiment of the concepts of the present invention uses a ball lens to transmit light of a particular wavelength into a capillary sample cell in a spectrofluorometer monitor. In this case, light of known wavelength emanates from a source, and a lens focuses the light onto a synthetic fused silica sphere (the ball lens) that is in contact with the capillary cell. The sphere concentrates the light as previously described. The light then passes into or through the inside bore of the capillary and the sample contained therein. In this embodiment another optical system using a sphere (ball lens) may be used to direct the fluorescence from the cell onto a wavelength selectable photodetector. The shape and size of the beams of light may be controlled by placement of one or more suitably shaped apertures on the optical axes. Sources, apertures, lenses and photodetectors are part of the fixed instrument, and the ball lenses and capillary are part of a removable cell assembly. If desired, apertures may be mounted on the removable cell assembly.

According to a further embodiment, the sample volume may be within the ball lens itself.

Accordingly, it is an object of the present invention to provide an improved spectroscopic instrument.

Another object of this invention is to provide an improved optical system for a sample cell.

A further object is to provide an apparatus and method for facilitating alignment of a sample cell in the optical path of a spectrophotometric monitor.

These and other objects and features of the present invention will become better understood through a consideration of the following description taken in conjunction with the drawings.

BRIEF DESCRIPTION OF THE DRAWINGS

FIGS. 1d and 1e respectively comprise a perspective schematic view of the monitor and an enlarged view of the relationship between the ball lens, capillary cell and detector;

FIGS. 3a and 3b illustrate a ring capillary cell assembly for mounting a ball lens according to the present invention in close proximity or direct contact with a capillary cell, with FIG. 3a being a plan view illustrating an elongated slot for receiving the capillary, and FIG. 3b a cross-sectional view along 3b—3b of FIG. 3a;

FIG. 4 is a schematic view of a further embodiment for a spectrofluorometer monitor;

DESCRIPTION OF THE PREFERRED EMBODIMENTS

Figure 1A:
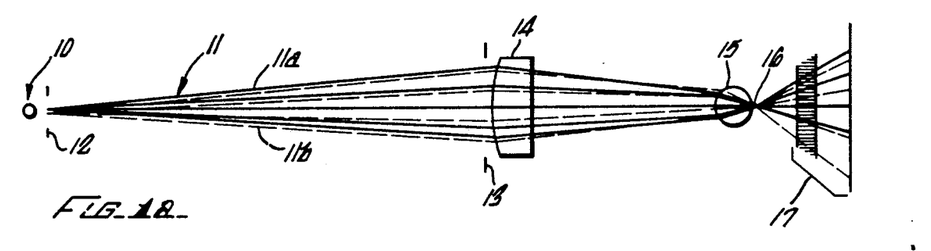
FIG. 1a is a schematic ray diagram of a ball lens microcell absorbance monitor in accordance with the present invention.
Figure 1B:
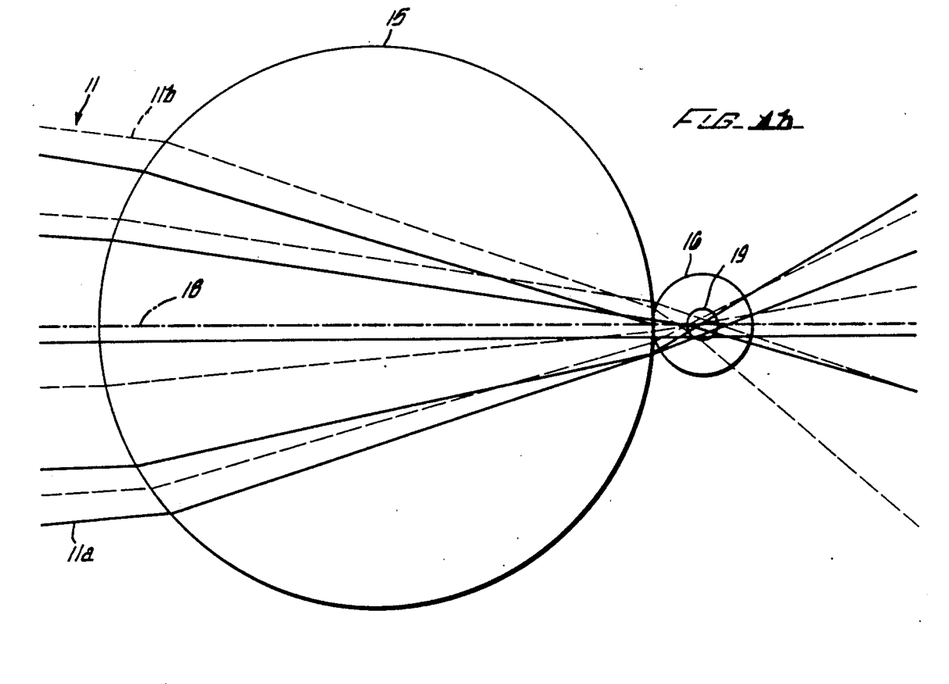
FIGS. 1b and 1c are enlarged views showing ray traces through the ball lens and capillary cell.
Figure 1C:
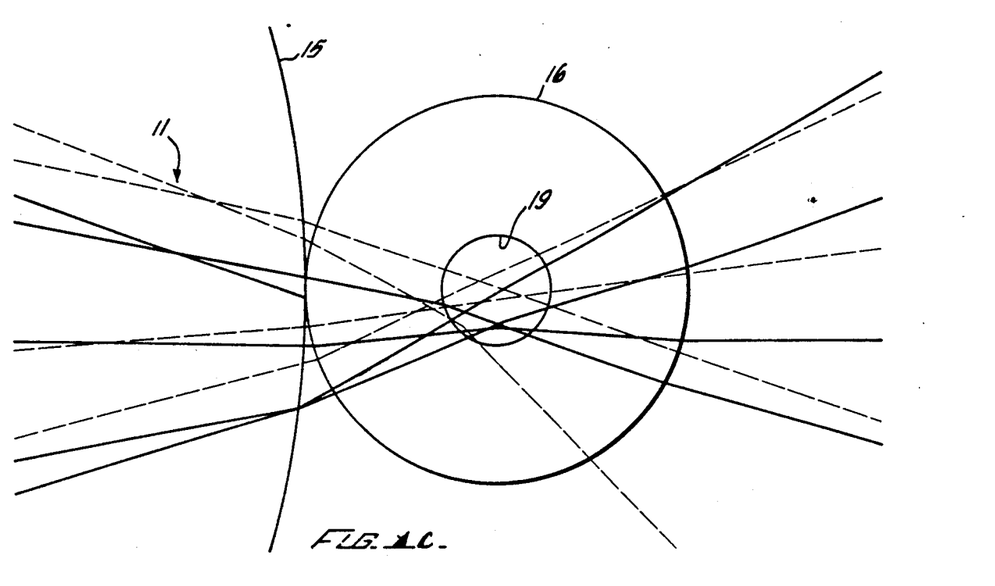
Figure 1D:
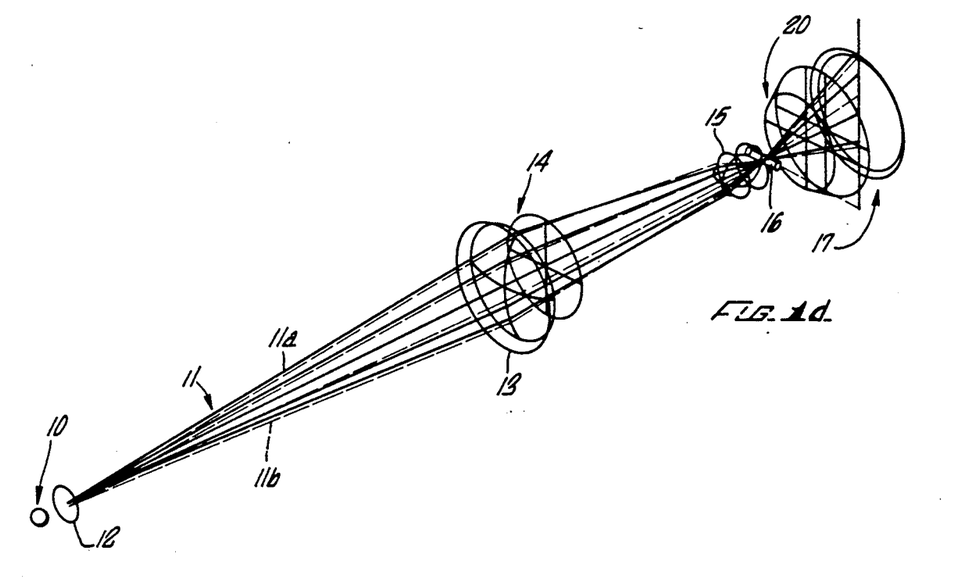

Turning now to the drawings, and first to FIG. 1, FIG. 1a is essentially a schematic ray diagram illustrating the basic concepts of an exemplary embodiment of the present invention. In FIG. 1a, a source 10 directs suitable radiation 11 through apertures 12 and 13, and a lens 14 to ball lens 15. Rays 11a represent rays from the edge of the source and rays 11b represent rays from the center of the source 10. The ball lens 15 is in direct contact with the outer wall of a capillary sample cell 16 spaced from the longitudinal axis of the cell as is better seen in FIGS. 1b, 1c and 1e. The light emanating from the inside bore of the cell 16 is directed to a suitable photodetector 17. FIGS. 1b, 1c and 1e are enlarged views and better illustrate the relationship of the ball lens 15 and the capillary 16, as well as the center line 18 (FIG. 1b) of the optical system of the monitor and the small diameter capillary bore 19 of the capillary cell 16. FIG. 1d includes an illustration of a window 20 which may be included on a typical sample cell.

As discussed previously, the ball lens can be a solid sphere or ball, solid cylinder, or truncated ball or cylinder, of transparent refractive material in a position such that a center line of the lens lies on a line extending from the source, or to a detector as the case may be, to the area of interest in a small volume (as more fully explained hereafter). The ball lens is preferably formed of a transparent material with an index of refraction greater than the surrounding area including but not limited to fused silia, sapphire, glass, and the like. In one exemplary embodiment, the ball lens is in direct contact with a capillary cell 16, or in an adjacent spaced relationship which provides suitable transmission of light through the sample cell (the small volume).

In an exemplary arrangement, the ball lens can have a diameter of two millimeters, wherein the capillary 16 has an outer diameter of 0.35 millimeter and an inside diameter of the bore 19 of 0.1 millimeter. It will be appreciated that the present invention is not limited to the above sizes, and others may be employed depending on application, instrument geometry and the like.

Figure 2A:
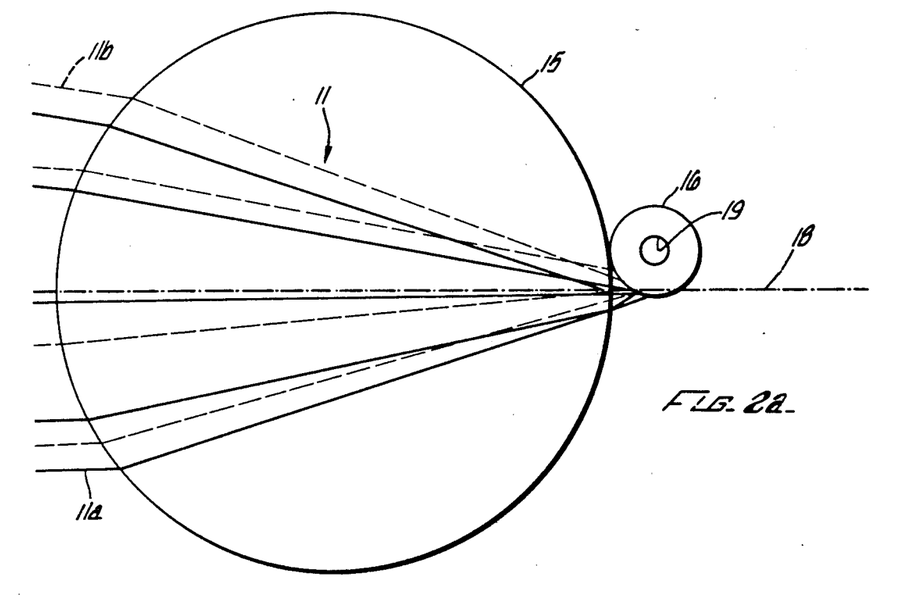
FIGS. 2a and 2b illustrate different effects of alignment, with FIG. 2a illustrating the ball lens as part of the monitor and separate from the cell on axis with the source beam and the capillary off axis, and FIG. 2b illustrating the effect where the ball lens and capillary are one unit and both off axis.
Figure 2B:
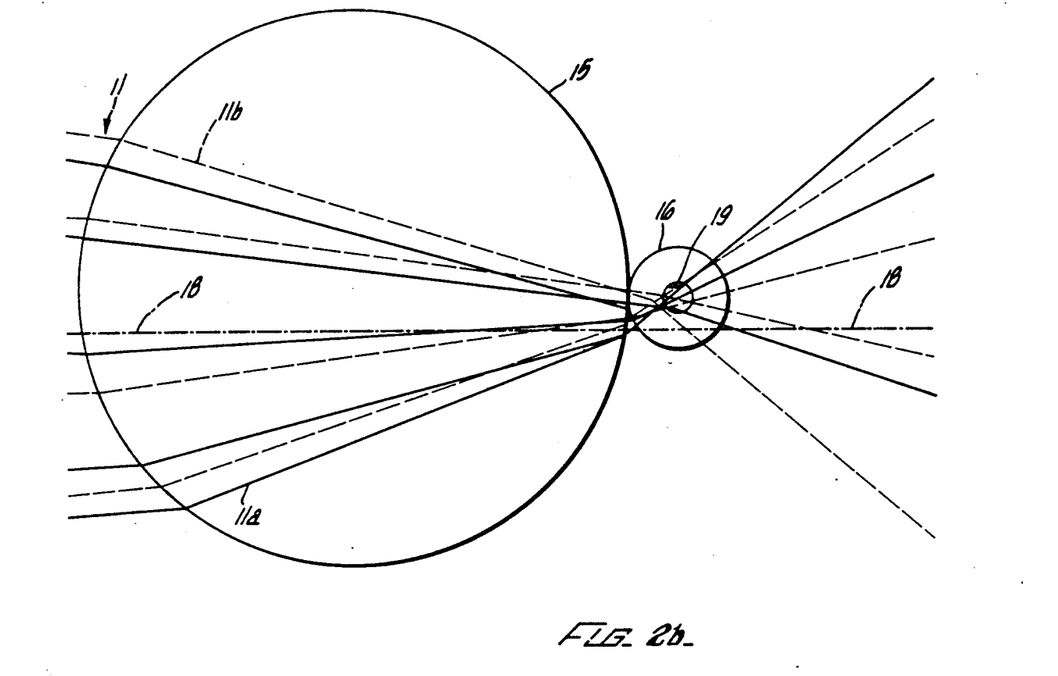

FIGS. 2a and 2b illustrate the problems respectively encountered and solved with the ball lens 15 as a part of the monitor (FIG. 2a) and as a part of the sample cell assembly (FIG. 2b). As shown in FIG. 2a, if the ball lens 15 is a part of the monitor and its optical system, as distinguished from being fixed with respect to the capillary cell 16, alignment is a significant problem. FIG. 2a illustrates the center line 18 of the optical system of the monitor and with the ball lens 15 on the center line, but with the capillary 16 off axis by 0.12 millimeter. Stated differently, the ball lens is on axis and the capillary is off axis. In this case, none of the rays 11 from the source hit the sample in the bore 19 of the capillary 16.

On the other hand, FIG. 2b illustrates an arrangement wherein the ball lens 15 and capillary 16 are fixed in an adjacent relationship according to the invention as a unit and separate from the monitor, and with both off axis by the same 0.12 mm amount. This FIG. 2b shows that where the capillary and ball lens are one unit, alignment with the center line of the monitor optical system is significantly less critical. This FIG. 2b shows that even with the ball lens 15 and capillary 16 off the monitor optical axis 18 by 0.12 mm, rays 11 from the source still pass through the bore 19 of the capillary 16.

Figure 3A:
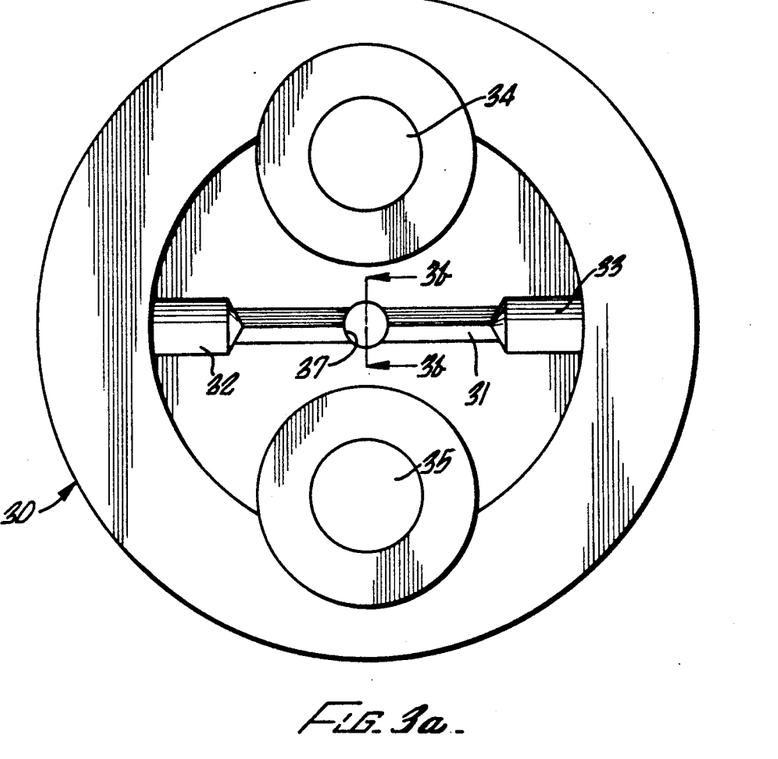
Figures 3B, 4:
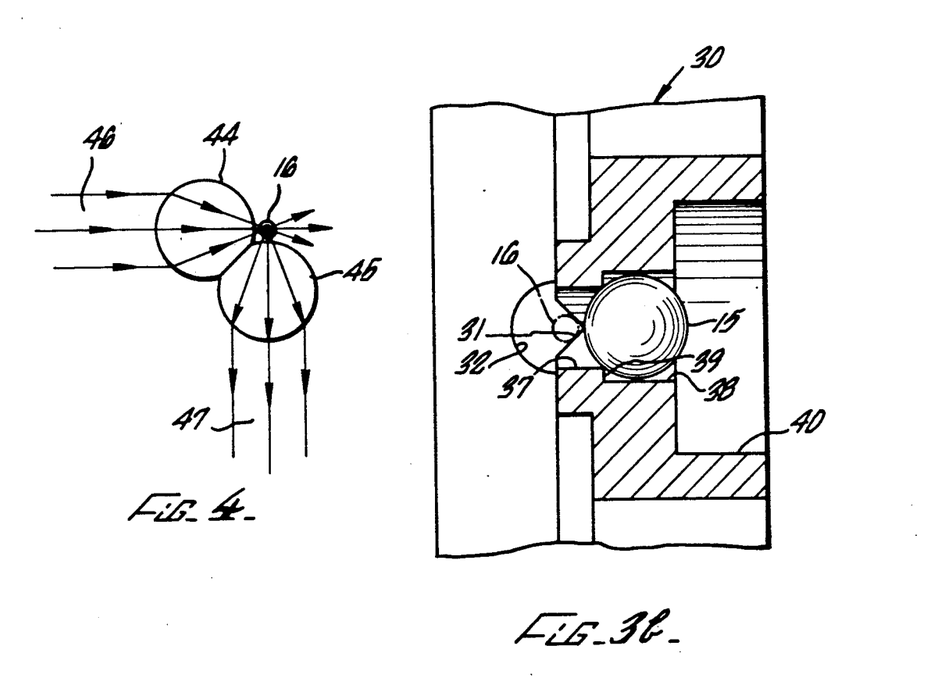

FIGS. 3a and 3b illustrate an exemplary plug or block assembly for mounting together a capillary and a ball lens, and comprise a block 30 having a locating notch in the form of a "V" groove 31 for receiving the capillary (shown by dashed lines 16), and with cavities 32, 33 for receiving end fittings (not shown) for the capillary. The block 30 has mounting holes 34, 35 for allowing the block, capillary and ball lens assembly to be mounted in a monitor.

The block 30 has a central bore or hole 37 through the block to allow radiation to pass therethrough and through the capillary and ball lens, and includes a further bore 38 which forms with the bore 37 a shoulder 39. These bores 37 and 38 are suitably configured such that the surface of the ball lens 15 extends to the end of the apex of the "V" groove 31 so as to be in close proximity or direct contact with the outer wall of the capillary 16. In the case of a cylinder lens 16, the bore 38 can be a suitably shaped slot. A further bore 40 may be provided so as to receive suitable mounting means (not shown) for holding the ball lens within the bore 38 and against the edge of the shoulder 39. For example, such mounting means can include a ring which firmly holds the ball lens 15 in place, or can include a resilient arrangement, such as a spring, to load the ball lens 15 in contact with the wall of the capillary 16. In an exemplary embodiment, the block 30 can have a diameter of 0.75 inch, a thickness of 0.250 inch, and a length of 0.30 inch for the groove 31. The bore 37 may be 0.055 inch diameter, the bore 38 0.082 inch diameter, and the bore 40 0.188 inch diameter, with the bore 37 having a length of 0.029 inch, and the bore 38 having a length of 0.051 inch.

FIG. 4 illustrates an alternative embodiment for a spectrofluorometer monitor comprising ball lenses in the form of a pair of truncated optical spheres 44 and 45 (or truncated optical cylinders likewise can be used) in contact with the capillary sample cell 16. In this arrangement, excitation radiation 46 from a suitable light source is directed toward the first sphere 44 and into the bore in the cell 16. In this embodiment, as previously noted, the excitation radiation 46 is of a suitable wavelength, and a lens or lenses (not shown) can be used to focus the radiation onto a synthetic fused silica (or other suitable material) sphere 44 that is in contact with the capillary cell 16. The sphere 44 concentrates the light which passes into or through the bore in the capillary and the sample contained therein. In this case, another optical system using the sphere 45 directs the fluorescence from the cell 16 onto a suitable wavelength selectable photodetector diagrammatically illustrated at 47. As will be apparent, the shape and size of the beams of radiation may be controlled by placement of one or more suitably shaped apertures on the optical axes. As with the preceding embodiment, the source, apertures, lenses and photodetector are part of the fixed instrument or monitor, and the spheres 44, 45 and capillary 16 are part of a removable cell assembly.

Figure 5A:
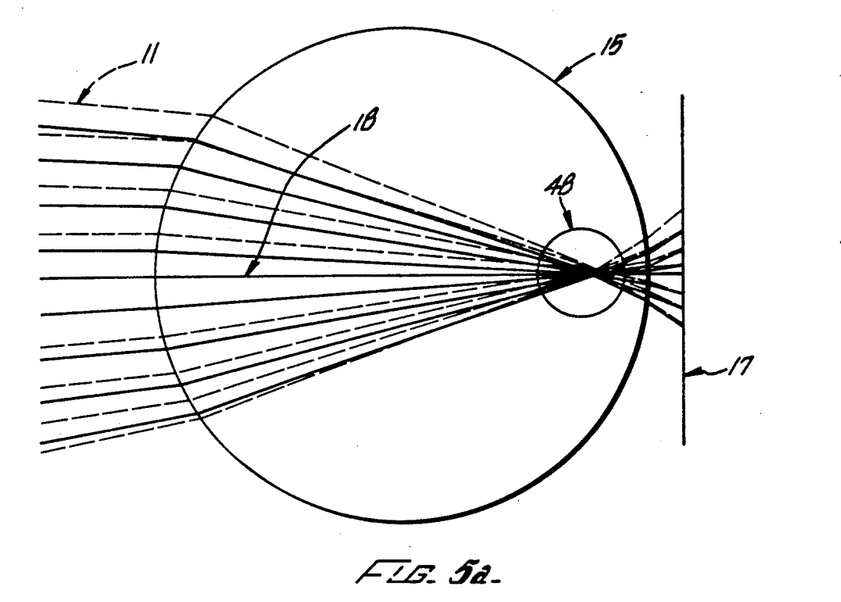
FIGS. 5a–5c are additional embodiments wherein a small sample volume is contained within a ball lens.

Another embodiment of the present invention is illustrated in FIG. 5a. Ball lens 15 includes a small volume cavity 48 off axis from the ball lens such that the center line 18 of the ball lens 15 lies on a line extending from the source 10, or from a detector 17, to the area of interest in the small volume 48. The small volume 48 can receive a sample to be analyzed.

Figure 5B:
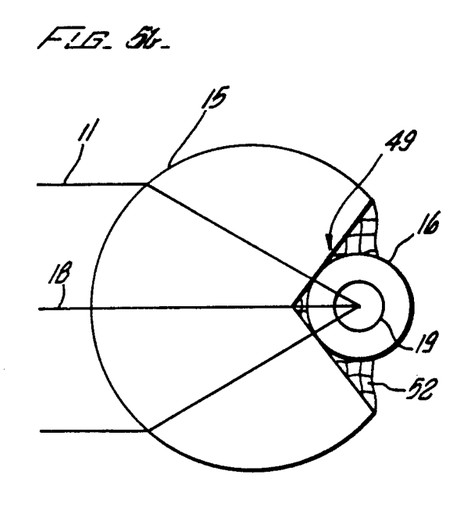
Figure 5C:
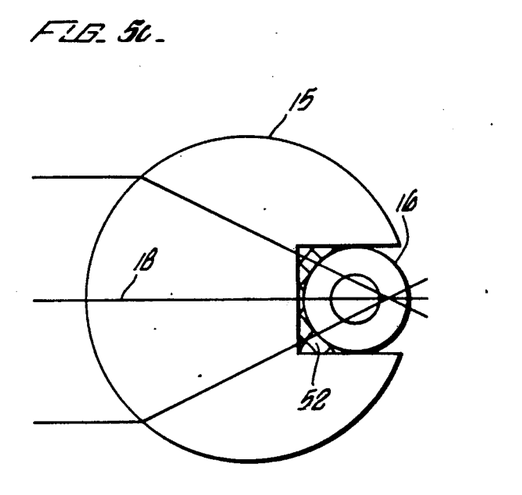

In another embodiment, as illustrated in FIG. 5b, a capillary 16 is made to pass through the ball lens 15 such that the bore 19 is in the desired off-axis position. This is achieved by forming a notch 49 in the ball lens 15 that allows for the passage and positioning of the capillary 16. The spaces between capillary 16 and ball lens 15 may be filled with a transparent material 52 of appropriate index of refraction to facilitate the desired transmission of light into the capillary bore 19. The notch may be a "V" groove or square groove, as illustrated in FIGS. 5b and 5c, or the like.

Figure 6A:
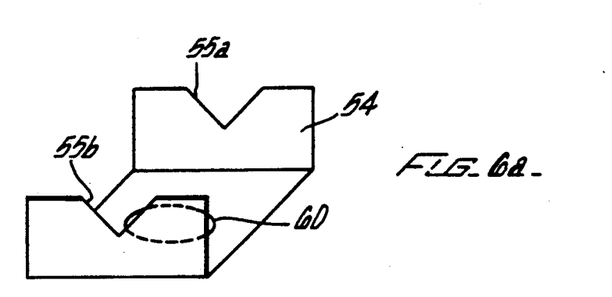
FIGS. 6a–c show a further alternative way of mounting a ball lens, with FIG. 6c being a cross-sectional view along line 6c—6c of FIG. 6b.
Figure 6B:
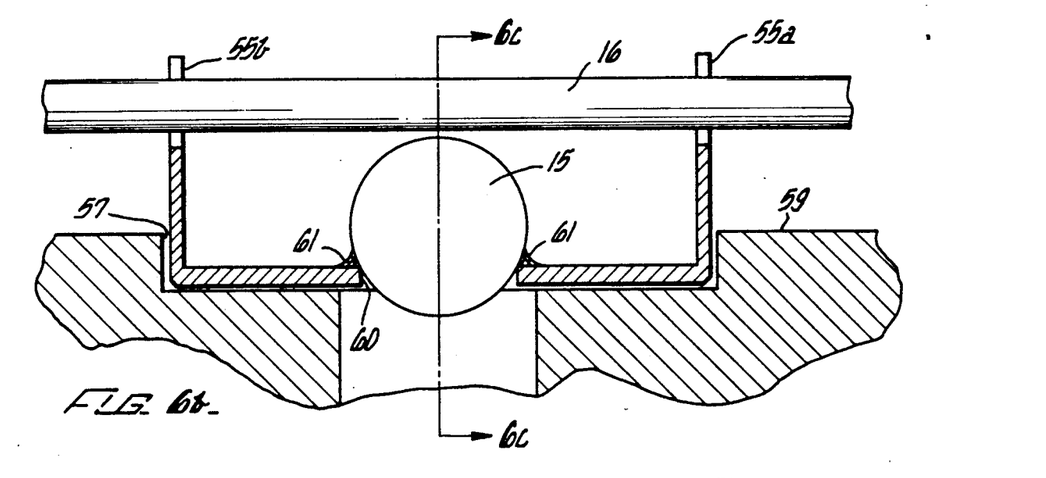
Figure 6C:
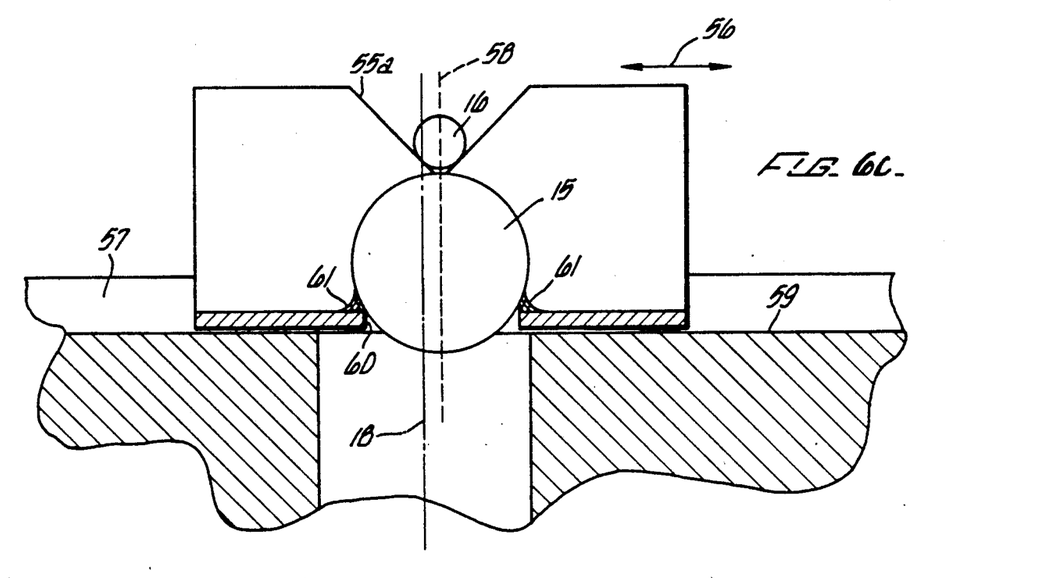

Another mounting embodiment is shown in FIG. 6 wherein the ball lens 15 is not fixed to the sample cell 16. The ball lens 15 is mounted in a ball lens holder element 54 which retains the ball lens and allows it to be moved in a slot 57 (see arrow 56) in a plane perpendicular to the optical axis 18 for alignment of the ball lens with the cell. The mounting element 54 has a groove, "V" notch or other retaining means 55a–b which registers against the wall of the capillary cell 16, aligning the axis 58, which is defined by the center of the ball lens and the center of the capillary, parallel with the optical axis 18. The cell 16 is fixed relative to the instrument 59, and the ball lens 15 can be held in an opening 60 of the element 54 by a suitable adhesive 61.

It is understood that the present invention is not restricted to any particular band in the electromagnetic spectrum, and is suitable, with the use of an appropriate dielectric material, to focus microwave radiation into a sample volume.

While embodiments of the present invention have been shown and described, various modifications may be made without departing from the scope of the present invention, and all such modifications and equivalents are intended to be covered.

What is claimed is:

1. A sample cell assembly for use in spectroscopy of samples in capillary chromatography comprising sample cell means having a cavity defined by a wall for containing a sample to be analyzed, and ball lens means in the form of a sphere mounted adjacent said wall for directing light from a source through said wall.

2. A sample cell assembly for use in spectroscopy for analysis of samples occupying small volumes comprising a ball lens in the form of a sphere mounted with respect to a source for directing light from the source to a sample volume of interest, and the sample volume of interest being contained in a capillary sample cell, said sphere being disposed adjacent a transparent wall of the sample cell.

3. A sample cell assembly for use in spectroscopy comprising
   a small volume sample cell comprising a capillary cell or the like and wherein the capillary cell is in the form of a hollow cylinder with a wall having an outer diameter larger than the diameter of a bore through the cylinder, and
   a ball lens in the form of a sphere mounted in close proximity and transverse to the outer surface of the wall of the capillary cell.

4. An assembly as in claim 3 wherein the ball lens is in a fixed relationship with respect to the wall of the cell.

5. An assembly as in claim 3 wherein said sphere comprises an optical sphere for collecting light from a source and directing the light to the cell for analyzing contents of a volume within said cell.

6. An assembly as in claim 3 further including a second ball lens mounted in close proximity to the outer wall of the cell for directing light from the cell.

7. A sample cell assembly for use in spectroscopy comprising sample cell having a cavity therein defined by a wall of the cell for containing a sample to be analyzed, and a sphere mounted adjacent said wall for directing light from the cavity to a detector.

8. An assembly as in claim 7 wherein said sample cell comprises a capillary cell.

9. Apparatus for use in spectroscopy for analyzing samples occupying small volumes, comprising
   a sample cell for containing a small volume of a substance to be analyzed and adapted to receive radiation from a source of finite extent directed to the volume, and wherein the volume has a cross-sectional area perpendicular to the optical axis between the source and the volume that is less than the cross-sectional area of the source, said cell having a solid transparent wall, and
   lens means for imaging the source into the volume at a magnification that substantially matches the size of the image to said cross-sectional size of the volume, wherein the numerical aperture of the foregoing optical system as viewed from the volume is greater than the numerical aperture as viewed from the source by a factor of one divided by a magnification of the lens means to thereby transfer light from the source to the volume with a low f/number lens system, and said lens means comprising a sphere lens disposed adjacent the wall of said cell.

10. A method of reducing the sensitivity to alignment of a sample cell in spectroscopy comprising the steps of
    forming an optical sample cell assembly including a sample cell and a ball lens in the form of a sphere, the cell having a bore for receiving a sample to be analyzed, and
    maintaining the ball lens in close proximity to the sample cell in optical alignment with the bore in the cell and for directing light from a source through the ball lens to the bore.

11. A sample cell assembly for use in spectroscopy comprising
    a small volume sample cell comprising a capillary cell or the like and wherein the capillary cell is in the form of a hollow cylinder with a wall having an outer diameter larger than the diameter of a bore through the cylinder,
    a ball lens mounted in close proximity to the outer surface of the wall of the capillary cell, and
    block means having an elongated locating notch in the form of a "V" groove for receiving the capillary cell therein, and including a bore therethrough for receiving the ball lens and maintaining the ball lens directly adjacent the wall of the cell.

12. A sample cell assembly for use in spectroscopy comprising
    a small volume sample cell comprising a capillary cell or the like and wherein the capillary cell is in the form of a hollow cylinder with a wall having an outer diameter larger than the diameter of a bore through the cylinder,
    a ball lens mounted in close proximity to the outer surface of the wall of the capillary cell, and
    block means having a "V" groove for receiving the capillary cell therein, and for supporting the ball lens in a movable relationship directly adjacent the wall of the cell.

13. A sample cell assembly for use in spectroscopy comprising
    a small volume sample cell comprising a capillary cell wherein the capillary cell is in the form of a hollow cylinder with a bore therethrough, and
    an optical sphere mounted in close proximity to the outer surface of the wall of the capacity cell for collecting light from a source and directing the light to the cell for analyzing contents of a volume within said cell.

14. A sample cell assembly for use in spectroscopy comprising
    a small volume sample cell comprising a capillary cell wherein the capillary cell is in the form of a hollow cylinder with a bore therethrough and
    an optical cylinder mounted in close proximity to the outer surface of the wall of the capillary cell for collecting light from a source and directing the light to the cell for analyzing contents of a volume within said cell.

* * * * *

Notice of Adverse Decisions in Interference

In Interference No. 102,792, involving Patent No. 5,037,199, L. Hlousek, BALL LENS MICROCELL, final judgment adverse to the patentees was rendered June 24, 1992, as to claims 1-5 and 7-13.

*(Official Gazette August 25, 1992)*